(12) United States Patent
McVicar et al.

(10) Patent No.: US 9,522,160 B2
(45) Date of Patent: Dec. 20, 2016

(54) OPHTHALMIC FORMULATIONS

(71) Applicant: Inotek Pharmaceuticals Corporation, Lexington, MA (US)

(72) Inventors: William K. McVicar, Sudbury, MA (US); Harun Takruri, Newport Beach, CA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 19 days.

(21) Appl. No.: 14/211,516

(22) Filed: Mar. 14, 2014

(65) Prior Publication Data

US 2014/0271876 A1   Sep. 18, 2014

Related U.S. Application Data

(60) Provisional application No. 61/793,273, filed on Mar. 15, 2013.

(51) Int. Cl.
| | |
|---|---|
| *A61K 31/7076* | (2006.01) |
| *A61K 31/14* | (2006.01) |
| *A61K 9/10* | (2006.01) |
| *A61K 45/06* | (2006.01) |
| *A61K 9/00* | (2006.01) |
| *A61K 31/5575* | (2006.01) |
| *A61K 47/38* | (2006.01) |

(52) U.S. Cl.
CPC .......... *A61K 31/7076* (2013.01); *A61K 9/0048* (2013.01); *A61K 9/10* (2013.01); *A61K 31/14* (2013.01); *A61K 31/5575* (2013.01); *A61K 45/06* (2013.01); *A61K 47/38* (2013.01)

(58) Field of Classification Search
CPC ...... A61K 31/7076; A61K 31/14; A61K 9/10; A61K 45/06; A61K 9/0048; A61K 31/5575; A61K 47/38
See application file for complete search history.

(56) References Cited

U.S. PATENT DOCUMENTS

| | | | |
|---|---|---|---|
| 3,819,613 A | 6/1974 | Kawazoe et al. |
| 3,832,341 A | 8/1974 | Duschinsky |
| 4,242,505 A | 12/1980 | Kawahara et al. |
| 4,849,311 A | 7/1989 | Itoh et al. |
| 4,968,697 A | 11/1990 | Hutchison |
| 5,140,015 A | 8/1992 | Olsson et al. |
| 5,206,222 A | 4/1993 | Forman et al. |
| 5,219,840 A | 6/1993 | Gadient et al. |
| 5,221,763 A | 6/1993 | Ueno et al. |
| 5,278,150 A | 1/1994 | Olsson et al. |
| 5,280,015 A | 1/1994 | Jacobson et al. |
| 5,296,504 A | 3/1994 | Stjernschantz et al. |
| 5,304,277 A | 4/1994 | Ohara et al. |
| 5,338,430 A | 8/1994 | Parsonage et al. |
| 5,407,793 A | 4/1995 | Del Nido et al. |
| 5,422,368 A | 6/1995 | Stjernschantz et al. |
| 5,443,836 A | 8/1995 | Downey et al. |
| 5,589,467 A | 12/1996 | Lau et al. |
| 5,591,887 A | 1/1997 | Ueno et al. |
| 5,604,210 A | 2/1997 | Nagaoka et al. |
| 5,620,676 A | 4/1997 | Jacobson et al. |
| 5,770,759 A | 6/1998 | Ueno et al. |
| 5,789,416 A | 8/1998 | Lum et al. |
| 5,801,159 A | 9/1998 | Miller et al. |
| 6,180,615 B1 | 1/2001 | Zablocki et al. |
| 6,214,807 B1 | 4/2001 | Zablocki et al. |
| 6,326,359 B1 | 12/2001 | Monaghan et al. |
| 6,358,536 B1 | 3/2002 | Thomas |
| 6,368,573 B1 | 4/2002 | Leung |
| 6,403,567 B1 | 6/2002 | Zablocki et al. |
| 6,403,649 B1 | 6/2002 | Woodward et al. |
| 6,407,076 B1 | 6/2002 | Box et al. |
| 6,426,337 B1 | 7/2002 | Cox et al. |
| 6,429,229 B1 | 8/2002 | Bouyssou et al. |
| 6,440,948 B1 | 8/2002 | Zablocki et al. |
| 6,448,236 B1 | 9/2002 | Monaghan et al. |
| 6,525,032 B2 | 2/2003 | Mantell et al. |
| 6,528,494 B2 | 3/2003 | Cox et al. |
| 6,528,516 B1 | 3/2003 | Civan et al. |
| 6,531,457 B2 | 3/2003 | Linden et al. |

(Continued)

FOREIGN PATENT DOCUMENTS

| | | |
|---|---|---|
| CN | 1164122 A | 11/1997 |
| CN | 101010085 A | 8/2007 |

(Continued)

OTHER PUBLICATIONS

Houlsby et al., Antimicrobial Agents and Chemotherapy 29: 803-806 (1986).*
Soulere, Laurent et al., "Synthesis and Uptake of Nitric Oxide-Releasing Drugs by the P2 Nucleoside Transporter in Trypanosoma equiperdum," Bioorganic & Medicinal Chemistry Letters, vol. 10:1347-1350 (2000).
Stewart, William C. et al., "Beta-Blocker-Induced Complications and the Patient With Glaucoma," Archives of Internal Medicine, vol. 158(3):221-226 (1998).
Stewart, William C., "Perspectives in the medical treatment of glaucoma," Current Opinion in Ophthalmology, vol. 10:99-108 (1999).
Sugrue, Michael F., "Pharmacological and Ocular Hypotensive Properties of Topical Carbonic Anhydrase Inhibitors," Progress in Retinal and Eye Research, vol. 19(1):87-112 (2000).

(Continued)

*Primary Examiner* — Sue Liu
*Assistant Examiner* — Thor Nielsen
(74) *Attorney, Agent, or Firm* — Nelsons Mullins Riley & Scarborough, LLP; Jane E. Remillard, Esq.; Cynthia L. Kanik

(57) ABSTRACT

The present invention relates to an ophthalmic formulation which comprises a fine particle of Compound A in an aqueous suspension and a manufacturing process thereof. More specifically, the present invention relates to a topically applied ophthalmic aqueous suspension which is obtainable by suspending fine particles of Compound A in an aqueous vehicle containing a surfactant and boric acid. The invention also provides processes for making the ophthalmic formulations and to methods of use thereof.

13 Claims, No Drawings

(56) References Cited

U.S. PATENT DOCUMENTS

| | | | |
|---|---|---|---|
| 6,534,486 B1 | 3/2003 | Allen et al. |
| 6,544,960 B1 | 4/2003 | Eldred et al. |
| 6,638,914 B1 | 10/2003 | Fishman et al. |
| 6,753,322 B2 | 6/2004 | Mantell et al. |
| 6,903,079 B2 | 6/2005 | Jagtap et al. |
| 6,921,753 B2 | 7/2005 | Mantell et al. |
| 7,084,127 B2 | 8/2006 | Van Tilburg et al. |
| 7,163,959 B2 | 1/2007 | Stjernschantz et al. |
| 7,189,706 B2 | 3/2007 | Van Tilburg et al. |
| 7,271,157 B2 | 9/2007 | Elzein et al. |
| 7,351,407 B2 | 4/2008 | Fleenor et al. |
| 7,423,144 B2 | 9/2008 | Jagtap et al. |
| 7,713,946 B2 | 5/2010 | Dhalla et al. |
| 7,732,424 B2 | 6/2010 | Jagtap et al. |
| 7,964,191 B2 | 6/2011 | Rodrigues et al. |
| 8,163,737 B2 | 4/2012 | Anderson et al. |
| 8,183,224 B2 | 5/2012 | Jagtap et al. |
| 8,207,215 B2 | 6/2012 | Muller et al. |
| 8,440,639 B2 | 5/2013 | Kim et al. |
| 8,455,457 B2 | 6/2013 | Kim et al. |
| 8,470,800 B2 | 6/2013 | Barman et al. |
| 8,476,247 B2 | 7/2013 | Kim et al. |
| 8,501,708 B2 | 8/2013 | Jagtap |
| 8,609,833 B2 | 12/2013 | Jagtap et al. |
| 8,648,169 B2 | 2/2014 | Saragovi |
| 8,784,886 B2 | 7/2014 | Fawzy et al. |
| 8,877,732 B2 | 11/2014 | Kim et al. |
| 8,895,530 B2 | 11/2014 | Kim et al. |
| 9,278,991 B2 | 3/2016 | McVicar |
| 9,289,383 B2 | 3/2016 | Kim et al. |
| 2001/0051612 A1 | 12/2001 | Cristalli |
| 2003/0013675 A1 | 1/2003 | Yeadon et al. |
| 2003/0055021 A1 | 3/2003 | DeNinno et al. |
| 2004/0166168 A1 | 8/2004 | Mathiowitz et al. |
| 2005/0250813 A1 | 11/2005 | Wieckhusen et al. |
| 2006/0009417 A1 | 1/2006 | Elzein et al. |
| 2006/0034941 A1 | 2/2006 | Dobson |
| 2007/0185051 A1 | 8/2007 | Dhalla et al. |
| 2007/0238694 A1 | 10/2007 | Salzman et al. |
| 2008/0050335 A1 | 2/2008 | Faour et al. |
| 2009/0131342 A1 | 5/2009 | Ellis |
| 2009/0220516 A1 | 9/2009 | Laties et al. |
| 2009/0258836 A1 | 10/2009 | Civan et al. |
| 2010/0041552 A1 | 2/2010 | Saxell et al. |
| 2010/0297121 A1 | 11/2010 | Mi |
| 2011/0123622 A1* | 5/2011 | Avery ............... A61K 9/0048 424/489 |
| 2011/0172177 A1* | 7/2011 | Kim ............... A61K 9/0048 514/46 |
| 2011/0217262 A1 | 9/2011 | Kornfield et al. |
| 2011/0245193 A1 | 10/2011 | Kim et al. |
| 2012/0108672 A1* | 5/2012 | Tsutsui ............... A61K 31/07 514/725 |
| 2013/0196940 A1 | 8/2013 | McVicar |
| 2014/0018314 A1 | 1/2014 | Kim et al. |
| 2014/0275128 A1 | 9/2014 | McVicar |
| 2015/0038448 A1 | 2/2015 | Kim et al. |
| 2015/0080330 A1 | 3/2015 | Kim et al. |

FOREIGN PATENT DOCUMENTS

| | | |
|---|---|---|
| CN | 101321460 A | 12/2008 |
| DE | 2342479 A1 | 3/1975 |
| EP | 0364417 A1 | 4/1990 |
| FR | 2186470 A1 | 1/1974 |
| GB | 2436255 A | 9/2007 |
| JP | 2012-508764 A | 4/2012 |
| KR | 20030005241 A | 1/2003 |
| WO | 9300329 A1 | 1/1993 |
| WO | 93/23418 A1 | 11/1993 |
| WO | 94/02497 A1 | 2/1994 |
| WO | 95/02604 A1 | 1/1995 |
| WO | 95/11681 A1 | 5/1995 |
| WO | 96/02553 A2 | 2/1996 |
| WO | 97/33590 A1 | 9/1997 |
| WO | 97/33879 A1 | 9/1997 |
| WO | 98/08855 A2 | 3/1998 |
| WO | 98/50047 A1 | 11/1998 |
| WO | 99/20284 A1 | 4/1999 |
| WO | 01/19360 A2 | 3/2001 |
| WO | 01/40245 A1 | 6/2001 |
| WO | 01/45715 A1 | 6/2001 |
| WO | 02/09702 A2 | 2/2002 |
| WO | 02/055085 A2 | 7/2002 |
| WO | 02/083152 A1 | 10/2002 |
| WO | 03/029264 A2 | 4/2003 |
| WO | 03/088978 A1 | 10/2003 |
| WO | 2005/117910 A2 | 12/2005 |
| WO | 2007/064795 A2 | 6/2007 |
| WO | 2008/130520 A1 | 10/2008 |
| WO | 2009/076580 A2 | 6/2009 |
| WO | 2009/100326 A1 | 8/2009 |
| WO | 2010/127210 A1 | 11/2010 |
| WO | 2011/077435 A1 | 6/2011 |
| WO | 2013/049725 A2 | 4/2013 |

OTHER PUBLICATIONS

Thompson, Robert D. et al., "Activity of N6-Substituted 2-Chloroadenosines at A1 and A2 Adenosine Receptors," J. Med. Chem., vol. 34:3388-3390 (1991).

Tian, Baohe et al., "Effects of Adenosine Agonists on Intraocular Pressure and Aqueous Humor Dynamics in Cynomolgus Monkeys," Exp. Eye Res., vol. 64:979-989 (1997).

Tsilimbaris, Miltiadis K. et al., "The Use of Atomic Force Microscopy for the Observation of Corneal Epithelium Surface," Invest. Ophthalmol. Vis. Sci., vol. 41:680-686 (2000).

Van Der Wenden, Eleonora M. et al., "5'-Substituted Adenosine Analogs as New High-Affinity Partial Agonists for the Adenosine A1 Receptor," J. Med. Chem., vol. 41:102-108 (1998).

Van Tilburg, Erica W. et al., "2,5'-Disubstituted Adenosine Derivatives: Evaluation of Selectivity and Efficacy for the Adenosine A1, A2A and A3 Receptor," J. Med. Chem., vol. 45:420-429 (2002).

Virág, László et al., "Effects of poly(ADP-ribose) polymerase inhibition on inflammatory cell migration in a murine model of asthma," Med. Sci. Monit., vol. 10(3):BR77-83 (2004).

Vitrori, Sauro et al., "2-Alkenyl and 2-Alkyl Derivatives of Adenosine and Adenosine-5'-N-Ethyluronamide: Different Affinity and Selectivity of E- and Z-Diastereomers at A2A Adenosine Receptors," J. Med. Chem., vol. 39:4211-4217 (1996).

Vitrori, Sauro et al., "N-Cycloalkyl Derivatives of Adenosine and 1-Deazaadenosine as Agonists and Partial Agonists of the A1 Adenosine Receptor," J. Med. Chem., vol. 43:250-260 (2000).

Viziano, Monica et al., "2-[N'-(3-Arylallylidene)hydrazino]adenosines Showing A2a Adenosine Agonist Properties and Vasodilation Activity," J. Med. Chem., vol. 38:3581-3585 (1995).

Witte, M.B. et al., "Nitric oxide enhances experimental wound healing in diabetes," British Journal of Surgery, vol. 89:1594-1601 (2002).

Woodward, D. et al., "Fixed-Combination and Emerging Glaucoma Therapies," Expert Opinion on Emerging Drugs, 2007, vol. 12, No. 2., pp. 313-327.

International Preliminary Report on Patentability, PCT/US2014/027662, dated Sep. 15, 2015, 8 pages.

Mitchell, C. et al., "The P2X7 Receptor in Retinal Ganglion Cells: A neuronal model of pressure-induced damage and protection by a shifting purinergic balance," Purinergic Signalling, vol. 4, pp. 313-321 (2008).

U.S. Appl. No. 14/552,160, N. Kim, filed Nov. 24, 2014, mailed Jul. 17, 2015.

U.S. Appl. No. 13/750,389, W. McVicar, filed Jan. 25, 2013, mailed Oct. 26, 2015.

U.S. Appl. No. 13/750,389, W. McVicar, filed Jan. 25, 2013, mailed May 21, 2015.

U.S. Appl. No. 14/211,567, W. McVicar, filed Mar. 14, 2014, mailed Oct. 26, 2015.

(56) References Cited

OTHER PUBLICATIONS

U.S. Appl. No. 14/211,567, W. McVicar, filed Mar. 14, 2014, mailed May 13, 2015.
U.S. Appl. No. 14/517,509, N. Kim, filed Oct. 17, 2014, mailed Sep. 11, 2015.
U.S. Appl. No. 14/517,509, N. Kim, filed Oct. 17, 2014, mailed Feb. 26, 2015.
U.S. Appl. No. 11/137,632, filed May 25, 2005, P. Jagtap.
U.S. Appl. No. 12/221,539, filed Aug. 4, 2008, P. Jagtap.
U.S. Appl. No. 13/451,613, filed Apr. 20, 2012, P. Jagtap.
U.S. Appl. No. 12/771,289, filed Apr. 30, 2010, P. Jagtap.
U.S. Appl. No. 13/004,380, filed Jan. 11, 2011, N. N. Kim.
U.S. Appl. No. 13/051,633, filed Mar. 18, 2011, N. N. Kim.
U.S. Appl. No. 13/051,655, filed Mar. 18, 2011, N. N. Kim.
U.S. Appl. No. 13/071,993, filed Mar. 25, 2011, P. Jagtap.
U.S. Appl. No. 13/072,349, filed Mar. 25, 2011, N. N. Kim.
U.S. Appl. No. 13/909,288, filed Jun. 4, 2013, N. N. Kim.
U.S. Appl. No. 14/552,160, filed Nov. 2, 2014, N. N. Kim.
U.S. Appl. No. 13/750,389, filed Jan. 25, 2013, W. McVicar.
U.S. Appl. No. 14/211,567, filed Mar. 14, 2014, W. McVicar.
U.S. Appl. No. 14/517,509, filed Oct. 17, 2014, N. N. Kim.
U.S. Appl. No. 11/137,632, Jun. 23, 2008.
U.S. Appl. No. 11/137,632, Nov. 8, 2007.
U.S. Appl. No. 11/137,632, May 9, 2007.
U.S. Appl. No. 12/221,539, Jan. 23, 2012.
U.S. Appl. No. 12/221,539, Sep. 2, 2011.
U.S. Appl. No. 12/221,539, Apr. 28, 2011.
U.S. Appl. No. 12/221,539, Sep. 22, 2010.
U.S. Appl. No. 13/451,613, Aug. 15, 2013.
U.S. Appl. No. 13/451,613, Dec. 17, 2012.
U.S. Appl. No. 12/771,289, May 16, 2013.
U.S. Appl. No. 12/771,289, Jan. 3, 2013.
U.S. Appl. No. 12/771,289, May 23, 2012.
U.S. Appl. No. 13/004,380, Jun. 24, 2014.
U.S. Appl. No. 13/004,380, Mar. 14, 2013.
U.S. Appl. No. 13/004,380, Sep. 10, 2013.
U.S. Appl. No. 13/051,633, Jan. 14, 2013.
U.S. Appl. No. 13/051,633, May 17, 2012.
U.S. Appl. No. 13/051,655, Feb. 4, 2013.
U.S. Appl. No. 13/051,655, May 16, 2012.
U.S. Appl. No. 13/071,993, Apr. 3, 2013.
U.S. Appl. No. 13/071,993, Jan. 8, 2013.
U.S. Appl. No. 13/071,993, Jun. 13, 2012.
U.S. Appl. No. 13/072,349, Mar. 4, 2013.
U.S. Appl. No. 13/072,349, Mar. 27, 2012.
U.S. Appl. No. 13/750,389, Sep. 23, 2014.
U.S. Appl. No. 13/909,288, Jul. 24, 2012.
U.S. Appl. No. 13/909,288, Jan. 2, 2014.
Haskó, György et al., "Adenosine Receptor Agonists Differentially Regulate IL-10, TNF-a, and Nitric Oxide Production in RAW 264.7 Macrophages and in Endotoxemic Mice," The Journal of Immunology, vol. 157:4634-4640 (1996).
Hirao, Mami et al., "Effects of adenosine on optic nerve head circulation in rabbits," Experimental Eye Research, vol. 79:729-735 (2004).
Homma, Hiroshi et al., "Nucleosides and Nucleotides. 112. 2-(1-Hexyn-1-yl)adenosine-5'-uronamides: A New Entry of Selective A2 Adenosine Receptor Agonists with Potent Antihypertensive Activity," J. Med. Chem., vol. 35:2881-2890 (1992).
Husain, S. et al., "Mechanisms Linking Adenosine A1 Receptors and Extracellular Signal-Regulated Kinase 1/2 Activation in Human Trabecular Meshwork Cells," The Journal of Pharmacology and Experimental Therapeutics, vol. 320(1):258-265 (2007).
Hutchison, Alan J. et al., "2-(Arylalkylamino)adenosin-5'-uronamides: A New Class of Highly Selective Adenosine A2 Receptor Ligands," J. Med. Chem., vol. 33:1919-1924 (1990).
International Search Report, PCT/US2014/27662, dated Jul. 21, 2014, 15 Pages.
Jacobson, Kenneth A. et al., "Adenosine receptors as therapeutic targets," Nature Reviews Drug Discovery, vol. 5:247-264 (2006).

Jagtap, Prakash G. et al., "2-(N-Acyl) and 2-N-acyl-N6-substituted analogues of adenosine and their affinity at the human adenosine receptors," Bioorganic & Medicinal Chemistry Letters, vol. 14:1495-1498 (2004).
Karl, Mike O. et al., "Differential P1-purinergic modulation of human Schlemm's canal inner-wall cells," Am. J. Physiol. Cell Physiol., vol. 288:C784-C794 (2005).
Kim, N. et al., "INO-8875, An Adenosine A1 Agonist, in Development for Open-Angle Glaucoma Reduces IOP in Three Rabbit Models," Investigative Ophthalmology & Visual Science, vol. 50, E-Abstract 4061 (2009).
Klotz, K.-N. et al., "Comparative pharmacology of human adenosine receptor subtypes—characterization of stably transfected receptors in CHO cells," Naunyn-Schmiedeberg's Arch. Pharmacol., vol. 357:1-9 (1998).
Klotz, Karl-Norbert et al., "Photoaffinity Labeling of A1-adenosine Receptors," The Journal of Biological Chemistry, vol. 260(27):14659-14664 (1985).
Knutsen, Lars J.S. et al., "N-Substituted Adenosines as Novel Neuroprotective A1 Agonists with Dimished Hypotensive Effects," J. Med. Chem., vol. 42:3463-3477 (1999).
Konno, Takashi et al., "2-(1-Hexyn-1-yl)adenosine-induced intraocular hypertension is mediated via K+ channel opening through adenosine A2A receptor in rabbits," European Journal of Pharmacology, vol. 518:203-211 (2005).
Konno, Takashi et al., "Effect of chymase on intraocular pressure in rabbits," European Journal of Pharmacology, vol. 524:132-137 (2005).
Konno, Takashi et al., "Involvement of Adenosine A2a Receptor in Intraocular Pressure Decrease Induced by 2-(1-Octyn-1-yl)adenosine or 2-(6-Cyano-1-hexyn-1-yl)adenosine," J. Pharmacol. Sci., vol. 97:501-509 (2005).
Kristinsson et al., Herbicidally Active Sulfamoyl Nucleosides: Isolation and Synthesis Synthesis and Chemistry of Agrochemicals IV, published 1995 by American Chemical Society, chapter 19, pp. 206-219.
Kunkel, Steven L. et al., "The role of chemokines in inflammatory joint disease," Journal of Leukocyte Biology, vol. 59:6-12 (1996).
Lesar, Timothy S., "Comparison of ophthalmic beta-blocking agents," Clinical Pharmacy, vol. 6:451-463 (1987).
Lichtenthaler, F.W. et al., "Nucleosides, XVIII. Improved Preparation of Nucleoside 5'-Nitrates," Synthesis, vol. 27:199-201 (1973).
Lohse, Martin J. et al., "8-Cyclopentyl-1,3-dipropylxanthine (DPCPX)—a selective high affinity antagonist radioligand for A1 adenosine receptors," Naunyn-Schmiedeberg's Arch. Pharmacol., vol. 336:204-210 (1987).
Mager, P.P. et al., "Molecular simulation applied to 2-(N'-alkylidenehydrazino)- and 2-(N'-aralkylidenehydrazino) adenosine A2 agonists," Eur. J. Med. Chem., vol. 30:15-25 (1995).
Maillard, Michel C. et al., "Adenosine Receptor Prodrugs: Synthesis and Biological Activity of Derivatives of Potent, A1-Selective Agonists," Journal of Pharmaceutical Sciences, vol. 83(1):46-53 (1994).
Matsuda, Akira et al., "Nucleosides and Nucleotides. 103. 2-Alkynyladenosines: A Novel Class of Selective Adenosine A2 Receptor Agonists with Potent Antihypertensive Effects," J. Med. Chem., vol. 35:241-252 (1992).
McKenzie, Sheila G. et al., "Effects of Adenosine and Related Compounds on Adenylate Cyclase and Cyclic AMP Levels in Smooth Muscle," European Journal of Pharmacology, vol. 41:193-203 (1977).
McWhinney, Charlene D. et al., "Activation of adenosine A3 receptors on macrophages inhibits tumor necrosis factor-a," European Journal of Pharmacology, vol. 310:209-216 (1996).
Mincione, Francesco et al., "The Development of Topically Acting Carbonic Anhydrase Inhibitors as Antiglaucoma Agents," Current Pharmaceutical Design, vol. 14:649-654 (2008).
Missiaen, Ludwig et al., "Effect of adenine nucleosides on myo-inositol-1,4,5-trisphosphate-induced calcium release," Biochem. J., vol. 325:661-666 (1997).
Moos, Walter H. et al., "N6-Cycloalkyladenosines. Potent A1-Selective Adenosine Agonists," Journal of Medicinal Chemistry, vol. 28(10):1383-1384 (1985).

(56) References Cited

OTHER PUBLICATIONS

Müller, C.E. et al., "Adenosine Receptor Ligands-Recent Developments Part I. Agonists," Current Medicinal Chemistry, vol. 7:1269-1288 (2000).
Nair, Vasu et al., "Novel, Stable Congeners of the Antiretroviral Compound 2',3'-Dideoxyadenosine," J. Am. Chem. Soc., vol. 111:8502-8504 (1989).
Nell, Peter G. et al., "The Adenosine A1 Receptor and its Ligands," Progress in Medicinal Chemistry, vol. 47:163-201 (2009).
Niiya, Kazunori et al., "2-(N'-Alkylidenehydrazino)adenosines: Potent and Selective Coronary Vasodilators," J. Med. Chem., vol. 35:4557-4561 (1992).
O'Neil et al. (eds.), "The Merck Index, 14th Edition," Merck & Co., Whitehouse Station, NJ, pp. 1693 (2006).
Ohno, Michihiro et al., "Modulation of adenosine receptor affinity and intrinsic efficacy in adenine nucleosides substituted at the 2-position," Bioorganic & Medicinal Chemistry, vol. 12:2995-3007 (2004).
Ongini, Ennio et al., "Pharmacology of adenosine A2A receptors," TiPS, vol. 17:364-372 (1996).
Orzalesi, Nicola et al., "Comparison of the Effects of Latanoprost, Travoprost, and Bimatoprost on Circadian Intraocular Pressure in Patients with Glaucoma or Ocular Hypertension," Ophthalmology, vol. 113:239-246 (2006).
Parmely, Michael J. et al., "Adenosine and a Related Carbocyclic Nucleoside Analogue Selectively Inhibit Tumor Necrosis Factor-a Production and Protect Mice against Endotoxin Challenge," The Journal of Immunology, vol. 151 (1):389-396 (1993).
Pitcher, Graham M. et al., "Paw withdrawal threshold in the von Frey hair test is influenced by the surface on which the rat stands," Journal of Neuroscience Methods, vol. 87:185-193 (1999).
Polska, Elzbieta et al., "Effects of Adenosine on Intraocular Pressure, Optic Nerve Head Blood Flow, and Choroidal Blood Flow in Healthy Humans," Investigative Ophthalmology & Visual Science, vol. 44(7):3110-3114 (2003).
Ralevic, Vera et al., "Receptors for Purines and Pyrimidines," Pharmacological Reviews, vol. 50(3):413-492 (1998).
Reinhart, Konrad et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," Crit. Care Med., vol. 24(5):733-742 (1996).
Reinstein, Leon J. et al., "Suppression of Lipopolysaccharide-stimulated Release of Tumor Necrosis Factor by Adenosine: Evidence for A2 Receptors on Rat Kupffer Cells," Hepatology, vol. 19:1445-1452 (1994).
Riché, Florence et al., "High tumor necrosis factor serum level is associated with increased survival in patients with abdominal septic shock: A prospective study in 59 patients," Surgery, vol. 120(5):801-807 (1996).
Rieger, Jayson M. et al., "Design, Synthesis, and Evaluation of Novel A2A Adenosine Receptor Agonists," J. Med. Chem., vol. 44:531-539 (2001).
Robinson, Ralph P. et al., "Discovery of the Humifumarate and (alpha-L-Alanyloxy)methyl Ether as Prodrugs of an Antirheumatic Oxindole: Prodrugs for the Enolic OH Group," J. Med. Chem., vol. 39:10-18 (1996).
Roelen, Harlof et al., "N6,C8-Disubstituted Adenosine Derivatives as Partial Agonists for Adenosine A1 Receptors," J. Med. Chem., vol. 39:1463-1471 (1996).
Sajjadi, Fereydoun G. et al., "Inhibition of TNF-a Expression by Adenosine," The Journal of Immunology, vol. 156:3435-3442 (1996).
Schleef, Raymond R. et al., "The Effect of Fibrin on Endothelial Cell Migration in Vitro," Tissue & Cell, vol. 14(4):629-636 (1982).
Shuman, Dennis A. et al., "The Synthesis of Nucleoside Sulfamates Related to Nucleocidin," Journal of the American Chemical Society, vol. 92(11):3434-3440 (1970).
Brown, M. R. W., et al., "The preservation of ophthalmic preparations," J. Soc. Cosmetic Chemists, vol. 16, pp. 369-393 (1965).

U.S. Appl. No. 15/044,705, filed Feb. 16, 2016, Norman N. Kim.
U.S. Appl. No. 15/005,697, filed Jan. 25, 2016, William K. McVivar.
U.S. Appl. No. 14/957,170, filed Dec. 2, 2015, William K. McVicar.
U.S. Appl. No. 13/750,389, Dec. 3, 2015.
U.S. Appl. No. 14/517,509, Feb. 18, 2016.
U.S. Appl. No. 14/211,516, Jan. 8, 2016.
U.S. Appl. No. 14/552,160, Nov. 12, 2015.
Accession No. 1994:153455, Higuchi, T. et al., "Evaluation of Serum Lactate-Dehydrogenase Activity for Estimation of Energy-Expenditure in Human-Subjects," Ergonomics, vol. 37(3):389-397 (1994).
Accession No. 2001:494425, Martin, H. et al., "The Guardian/Observer: Information developments since 1998," Aslib Proceedings, vol. 53(5):161-166 (2001).
Accession No. 2002:660483, Shore, G.M. et al., "eta '(eta)->gamma gamma: A tale of two anomalies," Physica Scripta, vol. T99:84-95 (2002).
Accession No. 2004:827690, Tacke, R. et al., "Sila-haloperidol: a silicon analogue of the dopamine (D-2) receptor antagonist haloperidol," Organometallics, vol. 23(19):4468-4477 (2004).
ACS Registry No. 151563-23-4 (1993).
ACS Registry No. 365533-72-8 (2001).
ACS Registry No. 365533-73-9 (2001).
ACS Registry No. 365533-74-0 (2001).
Al-Mughales, J. et al., "The chemoattractant activity of rheumatoid synovial fluid for human lymphocytes is due to multiple cytokines," Clin. Exp. Immunol., vol. 106:230-236 (1996).
Appel, S. et al., "Modelling of the pharmacodynamic interaction of an A1 adenosine receptor agonist and antagonist in vivo: N6-cyclopentyladenosine and 8-cyclopentyltheophylline," British Journal of Pharmacology, vol. 115:1253-1259 (1995).
Avila, M et al. British Journal of Pharmacology," A1-, A2a-, and A3-subtype adenosine receptors modulate intraocular pressure in the mouse," 2001, vol. 134, pp. 241-245.
Baraldi, Pier Giovanni et al., "Synthesis and Biological Activity of a New Series of N6-Arylcarbamoyl, 2-(Ar)alkynyl-N6-arylcarbamoyl, and N6-Carboxamido Derivatives of Adenosine-5'-N-ethyluronamide as A1 and A3 Adenosine Receptor Agonists," J. Med. Chem., vol. 41:3174-3185 (1998).
Bell, Jerald, A. et al., "Ocular Hypertension," eMedicine Ophthalmology, retreived online at: http://emedicine.medscape.com/article/1207470-overview (2008).
Beukers et al., "New, Non-Adenosine, High-Potency Agonists for the Human Adenosine A<SUB>2B </SUB>Receptor with an Improved Selectivity Profile Compared to the Reference Agonist N-Ethylcarboxamidoadenosine" J. Med. Chem., 2004, vol. 47, pp. 3707-3709.
Bouma, Maarten G. et al., "Differential Regulatory Effects of Adenosine on Cytokine Release by Activated Human Monocytes," The Journal of Immunology, vol. 153:4159-4168 (1994).
Bradley et al., "Purine Nucleoside-Dependent Inhibition of Cellular Proliferation in 1321N1 Human Astrocytoma Cells." J. Pharmacol. Expt. Ther., 2001, vol. 299, pp. 748-752.
Broadley, Kenneth J. et al., "Drugs modulating adenosine receptors as potential therapeutic agents for cardiovascular diseases," Exp. Opin. Ther. Patents, vol. 10(11):1669-1692 (2000).
Brooks, Anne M.V. et al., "Ocular beta-Blockers in Glaucoma Management, Clinical Pharmacological Aspects," Drugs & Aging, vol. 2(3):208-221 (1992).
Bruns, Robert F. et al., "Characterization of the A2 Adenosine Receptor Labeled by [3H]NECA in Rat Striatal Membranes," Biological Pharmacology, vol. 89:331-346 (1986).
Bruns, Robert F., "Adenosine receptor activation in human fibroblasts: nucleoside agonists and antagonists," Can. J. Physiol. Pharmacol., vol. 58:673-691 (1980).
Camaioni, Emidio et al., "Adenosine Receptor Agonists: Synthesis and Biological Evaluation of the Diastereoisomers of 2-(3-Hydroxy-3-phenyl-1-propyn-1-yl)NECA," Bioorganic & Medicinal Chemistry, vol. 5(12):2267-2275 (1997).
Cristalli, Gloria et al., "2-Alkynyl Derivatives of Adenosine and Adenosine-5'-N-ethyluronamide as Selective Agonists at A2 Adenosine Receptors," J. Med. Chem., vol. 35:2363-2368 (1991).

(56) References Cited

OTHER PUBLICATIONS

Cristalli, Gloria et al., "2-Alkynyl Derivatives of Adenosine-5'-N-ethyluronamide: Selective A2 Adenosine Receptor Agonists with Potent Inhibitory Activity on Platelet Aggregation," J. Med. Chem., vol. 37:1720-1726 (1994).

Cristalli, Gloria et al., "2-Aralkynyl and 2-Heteroalkynyl Derivatives of Adenosine-5'-N-ethyluronamide as Selective A2a Adenosine Receptor Agonists," J. Med. Chem., vol. 38:1462-1472 (1995).

Crosson, Craig E. et al., "Characterization of Ocular Hypertension Induced by Adenosine Agonists," Investigative Ophthalmology & Visual Science, vol. 37(9):1833-1839 (1996).

Crosson, Craig E. et al., "Modulation of Conventional Outflow Facility by the Adenosine A1 Agonist N6-Cyclohexyladenosine," Investigative Ophthalmology & Visual Science, vol. 46(10):3795-3799 (2005).

Crosson, Craig E. et al., "Modulation of Intraocular Pressure by Adenosine Agonists," Journal of Ocular Pharmacology, vol. 10(1):379-383 (1994).

Crosson, Craig E. et al., "Ocular effects associated with the chronic administration of the adenosine A1 agonist cyclohexyladenosine," Current Eye Research, vol. 21(4):808-813 (2000).

Crosson, Craig E., "Adenosine Receptor Activation Modulates Intraocular Pressure in Rabbits," The Journal of Pharmacology and Experimental Therapeutics, vol. 273(1):320-326 (1995).

Crosson, Craig E., "Intraocular Pressure Responses to the Adenosine Agonist Cyclohexyladenosine: Evidence for a Dual Mechanism of Action," Investigative Ophthalmology & Visual Science, vol. 42(8):1837-1840 (2001).

Crosson, Craig E., "Ocular hypotensive activity of the adenosine agonist (R)-phenylisopropyladenosine in rabbits," Current Eye Research, vol. 11(5):453-458 (1992).

Daines, Bradley S. et al., "Intraocular Adenosine Levels in Normal and Ocular-Hypertensive Patients," Journal of Ocular Pharmacology and Therapeutics, vol. 19(2):113-119 (2003).

Dalpiaz, Alessandro et al., "Development and characterization of biodegradable nanospheres as delivery systems of anti-ischemic adenosine derivatives," Biomaterials, vol. 26:1299-1306 (2005).

Dalpiaz, Alessandro et al., "Fabrication Via a Nonaqueous Nanoprecipitation Method, Characterization and in Vitro Biological Behavior of N6-Cyclopentyladenosine-Loaded Nanoparticles," Journal of Pharmaceutical Sciences, vol. 98 (11):4272-4284 (2009).

Dalpiaz, Alessandro et al., "Synthesis and Study of 5'-Ester Prodrugs of N6-Cyclopentyladenosine, a Selective A1 Receptor Agonist," Pharmaceutical Research, vol. 18(4):531-536 (2001).

De Lean, Andre et al., "Validation and Statistical Analysis of a Computer Modeling Method for Quantitative Analysis of Radioligand Binding Data for Mixtures of Pharmacological Receptor Subtypes," Molecular Pharmacology, vol. 21:5-16 (1982).

Deninno, Michael P. et al., "3'-Aminoadenosine-5'-uronamides: Discovery of the First Highly Selective Agonist at the Human Adenosine A3 Receptor," J. Med. Chem., vol. 46:353-355 (2003).

Elzein, Elfatih et al., "A1 adenosine receptor agonists and their potential therapeutic applications," Expert Opinion on Investigational Drugs, vol. 17(12):1901-1910 (2008).

Epple et al., "Solid-Phase Synthesis of Nucleoside Analogues" Journal of Combinatorial Chemistry (2003) vol. 5 pp. 292-310.

Fisher, Charles J. Jr. et al., "Treatment of Septic Shock with the Tumor Necrosis Factor Receptor : Fc Fusion Protein," N. Engl. J. Med., vol. 334(26):1697-1702 (1996).

Fleischhauer, J.C. et al., "Common Actions of Adenosine Receptor Agonists in Modulating Human Trabecular Meshwork Cell Transport," J. Membrane Biol., vol. 193:121-136 (2003).

Fleisher, David et al., "Improved oral drug delivery: solubility limitations overcome by the use of prodrugs," Advanced Drug Delivery Reviews, vol. 19:115-130 (1996).

Follmann, Hartmut et al., "Adenine Nucleosides in Solution: Circular Dichroism Studies and Base Conformation," Eur. J. Biochem., vol. 58:31-41 (1975).

Francis, John E. et al., "Highly Selective Adenosine A2 Receptor Agonists in a Series of N-Alkylated 2-Aminoadenosines," J. Med. Chem., vol. 34:2570-2579 (1991).

Fredholm, Bertil B. et al., "International Union of Pharmacology. XXV. Nomenclature and Classification of Adenosine Receptors," Pharmacological Reviews, vol. 53(4):527-552 (2001).

Frishman, William H. et al., "Topical Ophthalmic Beta-Adrenergic Blockade for the Treatment of Glaucoma and Ocular Hypertension," J. Clin. Pharmacol., vol. 34:795-803 (1994).

Gandolfi, Stefano et al., "Three-Month Comparison of Bimatoprost and Latanoprost in Patients With Glaucoma and Ocular Hypertension," Advances in Therapy, vol. 18(3):110-121 (2001).

Gurwood, Andrew S., "Comparing selective laser trabeculoplasty witih Latanoprost for the control of intraocular pressure," Br. J. Ophthalmol. vol. 89(11):1413-1417 (2005).

\* cited by examiner

OPHTHALMIC FORMULATIONS

RELATED APPLICATIONS

This application claims priority to U.S. Provisional Application No. 61/793,273, filed Mar. 15, 2013. The contents of any patents, patent applications, and references cited throughout this specification are hereby incorporated by reference in their entireties.

TECHNICAL FIELD

The present invention relates to an ophthalmic formulation which comprises fine particles of Compound A

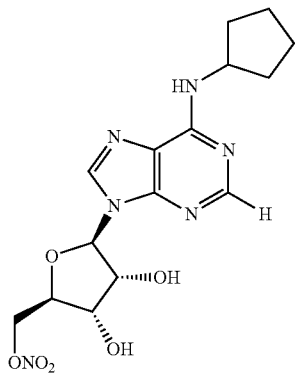

((2R,3S,4R,5R)-5-(6-(cyclopentylamino)-9H-purin-9-yl)-3,4-dihydroxytetrahydrofuran-2-yl)methyl nitrate, in an aqueous suspension and a manufacturing process thereof. More specifically, the present invention relates to a topically applied ophthalmic aqueous suspension which is obtainable by suspending a fine particle of Compound A in an aqueous vehicle containing a surfactant and boric acid at a pH between about 6.0 and 7.0, and to a method of reducing intraocular pressure or protecting retinal ganglion cells using the formulation.

BACKGROUND

US 2010-0279970A1, herein incorporated by reference in its entirety, discloses a clinically significant reduction of intraocular pressure using an Adenosine $A_1$ receptor agonist in human subjects having glaucoma.

US 2011-0123622A1, which is also incorporated by reference in its entirety as if individually set forth, describes formulations of Compound A comprising:

| Ingredient | % w/v |
| --- | --- |
| Compound A, micronized | 0.152-2.42 |
| Sodium CMC, low viscosity | 0.7 |
| Benzalkonium Chloride | 0.01 |
| Polysorbate 80 | 0.3 |
| Citric Acid Monohydrate | 0.15-0.3 |
| Glycine | 0-0.10 |
| NaCl | TBD (q.s. 270-300 mOsm) |
| NaOH/HCl (pH adjustment) | pH 5.1 ± 0.1 |
| Purified Water | q.s. 100.00 |

However, over time, there can be some variability in the chemical stability of these formulations at for example 25° Celsius, and, particle size growth can occur under some conditions in some of the formulations described in US 2011-0123622A1. Additionally, after prolonged storage of months to years, the suspended drug particles can settle to the bottom of the formulation making their re-suspension with shaking to re-form a homogeneous suspension difficult.

Accordingly, there exists a need to develop new ophthalmic formulations with (i) enhanced chemical stability, (ii) limited particle size growth over extended storage periods, and (iii) more rapid and efficient re-suspension of the active pharmaceutical ingredient (API) particles after storage. In addition, there exists a need to develop further ophthalmic formulations for delivering Compound A and a process for manufacturing the ophthalmic formulation.

SUMMARY OF INVENTION

The present invention is based, at least in part, on the discovery that formulations of Compound A containing boric acid have improved chemical stability and reduced particle growth during storage. In addition, these improved formulations have a lower surfactant concentration and a pH of 6.0 to 7.0 made possible by a phosphate buffer, which results in a flocculated suspension with improved re-suspension properties. Due to the pH range, the formulations are also better tolerated by patients and demonstrate improved compatibility with other ophthalmic agents (e.g., latanoprost), thereby facilitating co-formulation.

In a first aspect of the invention there is provided an ophthalmic formulation comprising:
(a) an aqueous suspension of micronized Compound A from 0.1 to 5.0% (w/v),
(b) a surfactant,
(c) boric acid from about 0.05 to about 2.0% (w/v), and
(d) a buffering agent that maintains the pH from about 6.0 to 7.0.

In one embodiment, the suspension of Compound A comprises fine particles with an X90 of less than about 25 microns. In another embodiment, the fine particles have an X90 less than about 10 microns. In a further embodiment, the fine particles have an X90 between about 3-7 microns.

In one embodiment, Compound A is present in the ophthalmic formulation between about 0.5 to about 5.0% (w/v). In another embodiment, Compound A is present in the ophthalmic formulation from about 1.0 to about 4.0% (w/v). In a further embodiment, Compound A is present in the ophthalmic formulation from about 2.0 to about 3.5% (w/v).

In one embodiment, the surfactant is selected from polysorbate 80, polysorbate 60, polysorbate 40, polysorbate 20, polyoxyl 40 stearate, poloxamers, tyloxapol and POE 35 castor oil. In one embodiment, the surfactant is polysorbate 80.

In one embodiment, the surfactant present in the ophthalmic formulation is between about 0.01 to about 0.5% (w/v). In another embodiment, the surfactant is present from about 0.01 to about 0.1% (w/v). In another embodiment the surfactant is present from about 0.01 to about 0.05% (w/v).

In another embodiment, the ophthalmic formulation further includes an osmolarity agent, such as sodium chloride. In one embodiment, the osmolarity agent is present from about 0.1% to 0.5% (w/v). In one embodiment the osmolarity agent is present at about 0.4%.

In another embodiment, the boric acid present in the ophthalmic formulation is about 0.5 to 1.0% (w/v). In one embodiment, the boric acid present in the ophthalmic formulation is about 0.8% (w/v).

In another embodiment, the formulation further includes a preservative between about 0.005 and about 0.05% (w/v). In one embodiment, the preservative is benzalkonium chloride present in the ophthalmic formulation between about 0.005 and about 0.02% (w/v). In a further embodiment, the benzalkonium chloride is present at about 0.01% (w/v).

In one embodiment, the formulation further includes a second intraocular pressure (IOP) reducing agent.

In one embodiment, the second IOP reducing agent is selected from the group comprising prostaglandin analogs, β-blockers, carbonic anhydrase inhibitors, rho-kinase inhibitors, $\alpha_2$ adrenergic agonists, miotics, neuroprotectants, adenosine $A_3$ antagonists, adenosine $A_1$ or $A_{2A}$ agonists, ion channel modulators and combinations thereof.

In one embodiment, the second IOP reducing agent is a prostaglandin analog.

In one embodiment, the second IOP reducing agent is latanoprost.

In one embodiment, the latanoprost is present between about 1-200 μg/ml.

In one embodiment, the latanoprost is present in about 50 μg/ml.

In another embodiment the buffering agent is a pharmaceutically acceptable phosphate buffer. In one embodiment, the phosphate buffer is present at about 10 mM. In another embodiment the, phosphate buffer is monobasic sodium phosphate present at about 0.1 to about 0.2% (w/v).

In another embodiment, the ophthalmic formulation further includes a suspending agent selected from sodium carboxymethylcellulose (NaCMC), hydroxyethylcellulose, hypromellose, polyvinyl alcohol, povidone, carbomers, hyaluronic acid and its salts, chondroitin sulfate and its salts, natural gums, and other pharmaceutically acceptable polymers. In one embodiment, the suspending agent is sodium carboxymethylcellulose (NaCMC). In another embodiment, the sodium carboxymethylcellulose (NaCMC) is present at about 0.07% w/v.

In a further embodiment, the pH of the formulation is about 6.5±0.1.

In a further embodiment, the formulation further includes edetate disodium. In one embodiment the edetate disodium is present between about 0.01 to about 0.1% (w/v). In another embodiment, the edetate disodium is present at about 0.015 to about 0.06% (w/v).

In one embodiment the formulation does not include glycine.

In one embodiment the ophthalmic formulation comprises

| Ingredient | %, w/v |
| --- | --- |
| Compound A, micronized | 0.4-5.0 |
| A suspending agent | 0.5-1.5 |
| Boric acid | 0.05-2.0 |
| A preservative | 0.005-0.05 |
| A surfactant | 0.01-0.1 |
| A phosphate buffering agent | 0.05-0.5 |
| NaCl | TBD (q.s. to 270-330 mOsm) |
| NaOH/HCl (pH adjustment) | pH 6.0-7.0 ± 0.1 |
| Purified Water | q.s. 100.00. |

In another embodiment the ophthalmic formulation comprises:

| Ingredient | %, w/v |
| --- | --- |
| Compound A, micronized | 0.5-3.0 |
| Sodium CMC, low viscosity | 0.7 |
| Boric Acid | 0.8 |
| Benzalkonium Chloride | 0.005-0.02 |
| Polysorbate 80 | 0.05 |
| Phosphate Buffer | 0.12 |
| edetate disodium | 0.015-0.06 |
| NaCl | 0.4 |
| NaOH/HCl (pH adjustment) | pH 6.5 ± 0.1 |
| Purified Water | q.s. 100.00. |

In one embodiment the ophthalmic formulation comprises:

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.015 |
| NaOH/HCl (pH adjustment) | pH 6.5 ± 0.1 |
| Purified Water | q.s. 100.00. |

In one embodiment the ophthalmic formulation comprises:

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.005 |
| Polysorbate 80 | 0.05 |
| Phosphate Buffer | 0.12 |
| edetate disodium | 0.03 |
| NaCl | 0.4 |
| NaOH/HCl (pH adjustment) | pH 6.5±0.1 |
| Purified Water | q.s. 100.00. |

In one embodiment the ophthalmic formulation comprises:

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.03 |
| NaCl | 0.4 |
| NaOH/HCl (pH adjustment) | pH 6.5 ± 0.1 |
| Purified Water | q.s. 100.00. |

In one embodiment the ophthalmic formulation comprises:

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.015 |
| Polysorbate 80 | 0.05 |

-continued

| Ingredient | %, w/v |
|---|---|
| Phosphate Buffer | 0.12 |
| edetate disodium | 0.03 |
| NaCl | 0.4 |
| NaOH/HCl (pH adjustment) | pH 6.5 ± 0.1 |
| Purified Water | q.s. 100.00. |

In one embodiment the ophthalmic formulation comprises:

| Ingredient | %, w/v |
|---|---|
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.06 |
| NaCl | 0.4 |
| NaOH/HCl (pH adjustment) | pH 6.5 ± 0.1 |
| Purified Water | q.s. 100.00. |

In one embodiment, the formulation further comprises a second ophthalmic agent. The second ophthalmic agent is selected from the group comprising: β-blockers, prostaglandin analogs, prostamides, carbonic anhydrase inhibitors, rho-kinase inhibitors, $\alpha_2$ adrenergic agonists, miotics, neuroprotectants, adenosine $A_1$ agonists, adenosine $A_3$ antagonists, adenosine $A_{2A}$ agonists and combinations thereof.

In one embodiment, the second agent is a prostaglandin analog selected from latanoprost, travoprost, unoprostone and bimatoprost.

In one embodiment, the prostaglandin analog is latanoprost.

In a further aspect, the present invention provides a method of reducing intraocular pressure comprising the step of: applying an effective amount of an ophthalmic formulation as defined above to an affected eye of a subject in need thereof.

In one embodiment the IOP of the affected eye is reduced by at least 10%. In another embodiment the IOP of the affected eye is reduced by at least 10-20%. In a further embodiment the IOP of the affected eye is reduced by 20% or more. In one embodiment the IOP of the affected eye is reduced by at least 10% for more than 3 hours, in another embodiment the IOP of the affected eye is reduced by at least 10-20% for more than 3 hours, in a further embodiment the IOP of the affected eye is reduced by 20% or more for more than 3 hours and in another embodiment the IOP of the affected eye is reduced by at least 10% for at least 6 hours. In one embodiment, the IOP of the affected eye is reduced by at least 20% for at least 12 hours. In one embodiment, the IOP of the affected eye is reduced by at least 20% for about 12 to about 24 hours.

In one embodiment, the ophthalmic formulation is administered to the affected eye of the subject in about 30 to about 50 µL drops.

In another embodiment, the ophthalmic formulation is administered in 1 to 2 drops once or twice daily.

In another embodiment, the subject has normal-tension glaucoma, OHT, or POAG.

In a further aspect, the present invention provides a method of treating retinal ganglion cell damage comprising the step of: applying an effective amount of an ophthalmic formulation as defined above to the affected eye of a subject in need thereof.

In one embodiment, the ophthalmic formulation is administered to the affected eye of the subject in about 30 to about 50 µl drops.

In another embodiment, the ophthalmic formulation is administered in 1 to 2 drops once or twice daily. In a further aspect, the present invention provides a method of preventing retinal ganglion cell damage comprising the step of: applying an effective amount of an ophthalmic formulation as defined above to an eye of a subject.

In one embodiment, the ophthalmic formulation is administered to the affected eye of the subject in about 30 to about 50 µl drops.

In another embodiment, the ophthalmic formulation is administered in 1 to 2 drops once or twice daily.

In a related embodiment, the methods as defined above further comprise the prior, simultaneous or sequential, application of a second opthalmic agent. In one embodiment the second ophthalmic agent is selected from the group comprising: β-blockers, prostaglandin analogs, prostamides, carbonic anhydrase inhibitors, rho-kinase inhibitors, $\alpha_2$ adrenergic agonists, miotics, neuroprotectants, adenosine $A_1$ agonists, adenosine $A_3$ antagonists, adenosine $A_{2A}$ agonists and combinations thereof.

In certain embodiments, the second agent is a prostaglandin analog selected from latanoprost, travoprost, unoprostone and bimatoprost. In one embodiment, the prostaglandin analog is latanoprost.

In a further aspect, there is provided a process for preparing a composition suitable for preparing ophthalmic formulations as described above comprising:
(a) micronizing Compound A into particle sizes of less than about 50 microns;
(b) suspending the particles of Compound A in an aqueous suspension with a surfactant and a buffering agent at a pH of about 6.0 to about 7.0;
(c) curing the product of step (b) at about 40° Celsius for between about 24 to about 96 hours; and
(d) adding a solution of boric acid from about 0.05 to about 2.0% (w/v) to provide a composition suitable for preparing ophthalmic formulations as described above.

In one embodiment, steps (a)-(c) are carried out at a volume less than the final volume of the ophthalmic formulation. In one embodiment, steps (a)-(c) are carried out at a volume of less than about 20% of the final volume of the formulation (and at about 5× the final excipient concentrations). In one embodiment, steps (a)-(c) are carried out at a volume of about 50% to about 85% of the final volume of the formulation (and at about 2× to 1.176× the final excipient concentrations, respectively). In one embodiment, steps (a)-(c) are carried out at a volume of about 75% of the final volume of the formulation (and at about 1.3× the final excipient concentrations).

In one embodiment, the process further comprises filtering the cured product of step (c) to a concentrated slurry prior to step (d). For example, a 0.22 micron filter can be used to reduce the volume of the cured solution without losing a significant portion of the suspended particles in step (c) prior to addition of the boric acid solution in step (d). Any reduction in volume at the end of step (c) would decrease the amount of impurities formed during curing which are dissolved in the suspending solution, and thus increase the purity of the final formulation.

In one embodiment, the resulting composition is sterilized. In another embodiment resulting composition is sterilized by gamma irradiation up to a maximum of 40 kGray (kGy) or by autoclaving.

In another embodiment the process is performed under aseptic conditions.

In another embodiment the resulting composition is diluted and the pH adjusted to produce an ophthalmic formulation as described above.

In one embodiment, the curing step takes place at about 40° Celsius for between about 48 to about 96 hours.

In another embodiment, the process includes the further step of adjusting the pH of the aqueous suspension to a pH of about 6.5±0.1.

In one embodiment, the final concentration of Compound A in the suspension is adjusted to between about 1 to about 50 mg/ml, or in another embodiment the final concentration of Compound A in the suspension is between about 3 to about 30 mg/ml. For example, in one embodiment, the formulation comprises about 0.1 to about 3.0% (w/v) of Compound A. In one embodiment, the formulation comprises about 0.5 to about 1.5% (w/v) of Compound A. In one embodiment, the formulation comprises about 3.0% (w/v) of Compound A.

In a further embodiment, the process of preparing the ophthalmic formulation comprises the addition of a second opthalmic agent. In one embodiment the second ophthalmic agent is selected from the group comprising: β-blockers, prostaglandin analog, prostamides, carbonic anhydrase inhibitors, rho-kinase inhibitors, $\alpha_2$ adrenergic agonists, miotics, neuroprotectants, adenosine $A_1$ agonist, adenosine $A_3$ antagonists, adenosine $A_{2A}$ agonists and combinations thereof.

In one embodiment, the second agent is a prostaglandin analog selected from latanoprost, travoprost, unoprostone and bimatoprost.

In one embodiment, the prostaglandin analog is latanoprost.

In a related aspect, there is provided a packaged topically applicable ophthalmic formulation comprising an aqueous suspension of fine particles of Compound A. In one embodiment, the packaged ophthalmic formulation is stable for at least 2 years at 5° Celsius and least 6 months at 25° Celsius. In one embodiment the packaged ophthalmic formulation is stable for about 12 to 18 months at 5° Celsius, and 3 to 6 months at 25° Celsius. In one embodiment the packaged ophthalmic formulation is stable at least 12 months at 5° Celsius and 3 months at 25° Celsius.

In one embodiment, the packaged formulation further comprises a second ophthalmic agent. In one embodiment, the packaged formulation further comprises latanoprost.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

DETAILED DESCRIPTION

Unless defined otherwise, all technical and scientific terms used herein have the same meaning as is commonly understood by one of skill in the art to which this invention belongs.

Definitions:

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

The term "surfactant" refers to a soluble compound that reduces the surface tension of liquids, or reduces interfacial tension between two liquids or a liquid and a solid, the surface tension being the force acting on the surface of a liquid, tending to minimize the area of the surface and facilitating the dispersion of a solid in a liquid.

The term "topical application" as used herein means application by way of a liquid, gel or ointment to the external corneal surface of a subject.

The term "subject" means a human subject or an animal subject (e.g., dogs, cats, cow, horses, pigs, sheep, goats, rabbits, guinea pigs, mice and rats).

The term "effective amount" as used herein refers to an amount of an ophthalmic formulation that is effective for at least one of the following: (i) treating or preventing elevated IOP; (ii) reducing IOP; (iii) treating or preventing retinal ganglion cell damage; and (iv) reducing retinal ganglion cell damage in a subject.

The term "treat" is used herein to mean to relieve, reduce or alleviate at least one symptom of a disease in a subject. For example, the term "treat" may mean to reduce or alleviate elevated intraocular pressure and/or to reduce or prevent further damage or loss of retinal ganglion cells. For example, treatment can be diminishment of one or several symptoms of a disorder or complete eradication of a disorder.

The terms "protect" or "prevent" are used interchangeably herein to delay the onset (i.e., the period prior to clinical manifestation of a disease) and/or to reduce the likelihood of a subject developing or worsening of a disease (e.g., a subject at risk of developing a disease). For example, the formulations of the invention may be used to prevent elevated intraocular pressure, and/or may be used as a neuroprotective composition to prevent retinal ganglion cell damage and/or retinal ganglion cell loss.

The particle size of the "fine particles" which may be used in the invention is preferably not more than about 50 microns, which is about the maximum particle size tolerated ophthalmically in topical formulations. The particle size may be between about 1 to about 50 microns, e.g., less than 50 microns, less than 40 microns, less than 30 microns, less than about 25 microns, less than 20 microns, or less than 10 microns, although it is to be appreciated that particle sizes of less than 1 micron are also acceptable. The particle sizes are defined as $X_{90}$ values, which refers to the particle size corresponding to 90% of the cumulative undersize distribution. In the present invention the $X_{90}$ of particles of Compound A is less than about 25 microns. The method of measuring particle sizes based on USP<429> "Light Diffraction Measurement of Particle Size"—available at www.pharmaceuticalonline.com/doc.mvc/utilizing-USP-429-mdash-light-diffraction-mea0001—has been employed by the applicants.

As used herein, the term "drop" refers to a quantity of ophthalmically acceptable fluid that resembles a liquid drop. In one embodiment, a drop refers to a liquid volume equivalent to about 5 μl to about 200 μl, e.g., about 30 μl to about 80 μl, e.g., about 30 μl to about 50 μl, e.g., about 35 μl.

The process for preparing the fine particles of Compound A may be carried out with any standard micronization techniques, including breakdown processes such as those using a ball mill, a bead mill, a jet mill, and a hammer mill; spray drying; as well as built-up processes such as crystallization (e.g., Rapid Expansion of Supercritical Solutions, RESS); SAS methods (Supercritical Anti-Solvent) and PGSS methods (Particles from Gas Saturated Solutions).

The surfactant of the invention is used as a wetting or dispersing agent to disperse and disaggregate the particles of the micronized Adenosine $A_1$ receptor agonist in the aqueous suspension formulation by wetting the surfaces of the particles to modulate their compatibility with the aqueous solution. The surfactant is selected from the group of surface active agents that are primarily nonionic and include without limitation polysorbate 80, polysorbate 60, polysorbate 40, polysorbate 20, polyoxyl 40 stearate, poloxamers, tyloxapol and POE 35 castor oil. It is to be appreciated that any similar pharmaceutically acceptable surface active agents may be usable at levels that do not cause irritation or discomfort when applied to the eye as topical drops.

The preservative of the invention is used to preserve the ophthalmic formulation upon storage and is required for multi-dose ophthalmic formulations. Suitable preservatives include quaternary ammonium salts such as benzalkonium chloride, cetrimide, chlorobutanol, sorbic acid, boric acid, edetate disodium and any other preservatives known to be safe and effective when used in topical ophthalmic products. The antimicrobial efficacy might be enhanced, especially with the quaternary ammonium salts, by the addition of chelating agents such as edetate disodium.

Suspending agents are used to increase the viscosity and reduce the settling rate of the micronized particles in suspension and to allow for uniform dosing by an end user. Suspending agents help to ensure uniformity in the manufacturing and filling processes. Suspending agents are primarily polymers that are synthetic, semi-synthetic, or natural, and include without limitation: soluble cellulose derivatives such as carboxymethylcellulose sodium (NaCMC), hydroxyethylcellulose, hypromellose and others; polyvinyl alcohol, povidone, carbomers, hyaluronic acid and its salts, chondroitin sulfate and its salts, natural gums, and other pharmaceutically acceptable polymers. It is important to note that these suspending agents might also provide some surfactant properties as noted above.

Buffering agents are used to maintain the pH during shelf life in the range most optimum to reduce the solubility of and therefore maintain the chemical stability of the suspended micronized particles of Compound A. A suitable buffering agent is a 10 mM phosphate buffer that is not irritating or discomforting to the eye.

As described in co-pending U.S. Provisional Application entitled "A Method of Providing Ocular Neuroprotection", filed Mar. 15, 2013, formulation of Compound A have been shown to have a neuroprotective effect on retinal ganglion cells. Accordingly, the ophthalmic formulations are useful for the treatment or prevention of retinal neuropathies and neurodegenerative conditions of the eye including, but not limited to, glaucoma (e.g., pseudo-exfoliative and pigment dispersion glaucoma, and closed angle glaucoma), ocular ischemic syndrome, retinal ischemia (e.g., retinal hypoxia ischemia), retinal vein occlusion, diabetic retinopathy, trauma (e.g., Purtsher's retinopathy), age-related macular degeneration, visual loss form retinal detachment and other conditions resulting in increased permeability of the blood-retinal barrier (BRB) resulting in fluid accumulation and retinal edema.

There are a number of methods which can be used to measure the function of retinal ganglion cells. For example, damage to retinal ganglion cells can be measured using the following techniques:

(i) measurement of visual field loss. Visual field loss and its progression are hallmarks in glaucoma, including normal tension glaucoma, and high IOP glaucoma, optic neuritis and retinal ganglion cell damage. Visual filed loss can be measured using various perimetery techniques. Visual field loss measurements can be very useful in finding early changes in vision caused by RGC damage.

(ii) electroretinogram (ERG) or electroretinography measurements provide information on damage to RGC. Electroretinography measures electrical activity generated by the photoreceptor cells in the retina when the eye is stimulated by certain light sources. The measurement is captured by electrodes placed on the front surface of the eye (e.g. cornea) and the skin near the eye and a graphic record called an electroretinogram (ERG) is produced. Electroretinography is useful in diagnosing several hereditary and acquired disorders of the retina, damage to retinal ganglion cells by conditions such as but not limited retinitis pigmentosa, a detached retina or functional changes caused by arteriosclerosis or diabetes. In particular, the photopic negative response (PhNR) of an ERG is thought to measure the presence of intact, functioning RGCs (Viswanathan S, Frishman L J, Robson J G, et al. The photopic negative response of the macaque electroretinogram: reduction by experimental glaucoma. Invest Ophthalmol Vis Sci. 1999; 40:1124-1136), and this signal has been shown to correlate to visual field loss in patients with glaucomatous vision field loss (Viswanathan S, Frishman L J, Robson J G, Walter J W. The photopic negative response of the flash electroretinogram in primary open angle glaucoma. Invest Ophthalmol Vis Sci. 2001; 42:514-522), (iii) retinal nerve fiber layer thickness (RNFL) measurements, measured by optical coherence tomography or scanning laser polarimetry as reported in Tsai J C, Chang H W. Comparison of the effects of brimonidine 0.2% and timolol 0.5% on retinal nerve fiber layer thickness in ocular hypertensive patients: a prospective, unmasked study. *J OculPharmacolTher.* 2005; 21:475-82.

Subjects that are susceptible to or at risk of developing RGC damage would be candidates for employing the preventative methods of the invention are subjects having a family history of glaucoma (e.g., normal tension glaucoma, pseudo-exfoliative and pigment dispersion glaucoma, and closed angle glaucoma), subjects that have a family history of visual field loss; subjects that have a family history of ocular ischemic syndrome, retinal ischemia (e.g., retinal hypoxia ischemia), retinal vein occlusion, retinal artery occlusion, diabetic retinopathy, age-related macular degeneration, visual loss from retinal detachment, conditions resulting in increased permeability of the blood-retinal barrier (BRB) resulting in fluid accumulation and retinal edema; subjects that are to face ocular surgery or have experienced ocular trauma; as well as subjects that have ocular diseases or diseases associated with the development of retinal ganglion cell damage including glaucoma (e.g., normal tension glaucoma, pseudo-exfoliative and pigment dispersion glaucoma, and closed angle glaucoma), diabetes, malignancy, infection, ocular ischemia, ocular inflammation, ocular compression, elevated intraocular pressure, interruption in the blood circulation to the retinal ganglion cells, ocular ischemic syndrome, retinal ischemia (e.g., retinal hypoxia ischemia), retinal vein occlusion, retinal artery occlusion, diabetic retinopathy, age-related macular degeneration, visual loss from retinal detachment, conditions resulting in increased permeability of the blood-retinal barrier (BRB) resulting in fluid accumulation and retinal edema, or combinations thereof. Where discrepancies exist between a compound's name and a compound's structure, the chemical structure will control.

The ophthalmic formulations are administered to in amounts sufficient to lower IOP and/or to reduce retinal ganglion damage or loss in subjects experiencing elevated IOP or retinal ganglion cell damage or loss; and/or to maintain normal IOP levels and/or prevent retinal ganglion cell loss in subjects at risk of developing IOP or retinal ganglion cell damage or loss.

Thus, for topical presentation 1 to 2 drops of these formulations would be delivered to the surface of the eye from 1 to 4 times per day, according to the discretion of a skilled clinician.

The ophthalmic formulations can also be used in combination with other glaucoma treatment agents, such as, but not limited to, β-blockers, prostaglandin analogs, prostamides, carbonic anhydrase inhibitors, $\alpha_2$ adrenergic agonists, miotics, and neuroprotectants, adenosine $A_1$ agonists, adenosine $A_3$ antagonists, adenosine $A_{2A}$ agonists and combinations thereof. As used herein, a "combination of agents" and similar terms refer to a combination of two types of agents: (1) adenosine receptor $A_1$ agonists (e.g. compounds of Formula I) and/or pharmacologically active metabolites (e.g., cyclopendyladenosine), salts, solvates and racemates of adenosine receptor $A_1$ agonists and (2) prostaglandin analogs (e.g. latanoprost) and/or pharmacologically active metabolites, salts, solvates and racemates of prostaglandin analogs. Pharmacologically active metabolites include those that are inactive but are converted into pharmacologically active forms in the body after administration.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

The optimal dose of the combination of agents use in the methods described herein can be determined empirically for each individual using known methods and will depend upon a variety of factors, including, though not limited to, the degree of advancement of the disease; the age, body weight, general health, gender and diet of the individual; the time of administration; and other medications the individual is taking. Optimal dosages may be established using routine testing and procedures that are well known in the art. Daily dosages for the compounds of formula I can be 10 μg to about 2000 μg.

Frequency of dosage may vary depending on the formulation used and the particular condition to be treated or prevented and the patient's/subject's medical history. In general, the use of the minimum dosage that is sufficient to provide effective therapy is preferred. Patients may generally be monitored for therapeutic effectiveness using assays or tests suitable for monitoring IOP or retinal damage for the condition being treated or prevented, which will be familiar to those of ordinary skill in the art.

The following abbreviations are used herein and have the indicated definitions: IOP is intraocular pressure; OHT is ocular hypertension; POAG is primary open-angle glaucoma; and NaCMC is sodium carboxymethylcellulose.

EXAMPLES

The present invention is further illustrated by the following examples, but should not be construed to be limited thereto.

Example 1

Synthesis of Compound A

The following Scheme 1 shows the reaction scheme in the preparation of Compound A. The GMP preparation of Compound A is described in detail.

The quantities detailed are calculated for a production batch of approximately 40 g of Compound A. The production described can be scaled up.

Step 1: 1 Liter of ethanol was charged into a reactor and stirred rapidly. 0.3 kg of 6-chloroadenosine and 0.267 Kg of cyclopentylamine were added to the ethanol in the reactor. The reactor was heated to reflux for 2 hr, then cooled to 8° C. and kept under these conditions for 12 hours. The crystallized material was filtered from the mother liquid and the solid cake was washed with 0.33 L of ethanol to produce a wet cake. The wet cake was dried to obtain N6-cyclopentyladenosine (0.249 Kg).

Step 2: Dimethoxypropane was used to protect the 2' and 3' hydroxyl groups on the sugar unit. 3.7 liters of acetone was charged into the reactor and was stirred rapidly. 0.249 Kg of N6-cyclopentyladenosine; 0.386 Kg of dimethoxypropane and 0.148 Kg of p-toluenesulfonic acid were added to the acetone (3.7 L) in the reactor. The reactor was heated to 40° C. for 1.5 hours. The solvents were then removed by distillation under vacuum at 40° C. to prepare a dry crude material. 3.1 L of ethyl acetate were then added to the dry crude material obtained. The solution was then cooled to 6° C. and 0.5N NaOH solution was added by dripping until a pH of 8 was reached. This equated to approximately 1.55 L of NaOH solution. After the phase separation was complete, 0.78 L of saturated sodium chloride 20% solution was added to the organic phase. 0.78 L of saturation sodium chloride 20% solution was added again. The two phases were stirred for 30 minutes. The organic phase that was ethyl acetate based was separated and dried with 0.157 Kg of sodium sulphate and washed with 1 L of ethyl acetate. The solution was filtered and evaporated to an oil under vacuum at 55° C. To the remaining oil 1.2 L of hexane and 0.3 L of ethyl acetate were added. The reaction mixture was heated to 55° C. for 3 hours and then the solution was cooled to 5° C. and maintained at this temperature for 12 hours. The solids were filtered and the resulting cake was washed with a 0.625 L of ethyl acetate:hexane (1:4) solution. After drying the solid 140 g of 2',3'-isopropylidene-N$^6$-cyclopentyl adenosine was obtained.

Step 3: Nitration of the 5' position of 2',3'-isopropylidene-N$^6$-cyclopentyl adenosine obtained in Step 2 was carried out with a nitric acid acetic anhydride mixture. 0.127 L of dichloromethane was charged into the reactor and stirred rapidly. 140 g of 2',3'-isopropylidene-N$^6$-cyclopentyl adenosine was added and the reaction solution was cooled to −20° C. 0.547 L of a solution composed of 0.127 L nitric acid 65% in 0.420 L of acetic anhydride was added at a rate that kept the reaction mixture below −15° C., the temperature range of between −23 to −18° C. has been found to be the preferred target range. If the temperature increases then impurities were found to be generated. The addition of the acid mixture took about 0.5 hr. The mixture was stirred for 20 mins and then quenched into 0.35 L of cold saturated sodium bicarbonate solution. The pH was corrected to 7 by the addition of solid sodium bicarbonate to the aqueous later. The organic phase was separated and the aqueous layer extracted with 0.4 L of dichloromethane. The organic phases were combined and washed with 0.6 L of saturated sodium chloride solution. The organic phase containing 2',3'-isopropylidene-N$^6$-cyclopentyladenosine-5'-nitrate was then separated for use in Step 4 below.

Step 4: Because of its liability the protected 2',3'-isopropylidene-N$^6$-cyclopentyladenosine-5'-nitrate was hydrolyzed directly without purification. The solution from Step 3 was evaporated at 20° C. under vacuum to an oil. The oil was cooled to less than 2° C. 1.95 L of trifluoroacetic acid:water (3:1) solution was added. The reaction mixture was stirred for 0.5 hours and allowed to warm to room temperature while being stirred. After that, the sodium bicarbonate solution was prepared and cooled to less than 10° C. The sodium bicarbonate solution was added to the reaction mixture to quench the reaction. The ethyl acetate was added to the reaction vessel and the pH was adjusted and the organic layer was worked up and dried with sodium sulfate. The resulting product solution was then dried several times with magnesium sulphate and the material stripper to form crude Compound A.

The crude compound A was then recrystallized from ethanol. The crude compound A material was dissolved in ethanol then concentrated to half volume to crystallize for 36 hours. After that the resulting product was isolated by filtration to provide Compound A. $^1$H-NMR (DMSO-d$_6$): δ 1.49-1.58 (m, 4H), 1.66-1.72 (m, 2H), 1.89-1.94 (m, 2H), 4.12-4.17 (m, 1H), 4.28-4.33 (m, 1H), 4.48 (bs, 1H), 4.65-4.87 (m, 3H), 5.5 (d, J=5.1 Hz, 1H), 5.63 (d, J=5.7 Hz, 1H), 5.91 (d, J=5.1 Hz, 1H), 7.75 (d, J=7.5 Hz, 1H), 8.17 (bs, 1H), 8.30 (s, 1H); MS (ES$^+$): m/z 381.35 (M+1); Anal. Calcd for C$_{15}$H$_{20}$N$_6$O$_6$: C, 47.37; H, 5.30; N, 22.10. Found: C, 47.49; H, 5.12, N, 21.96.

Scheme 1:

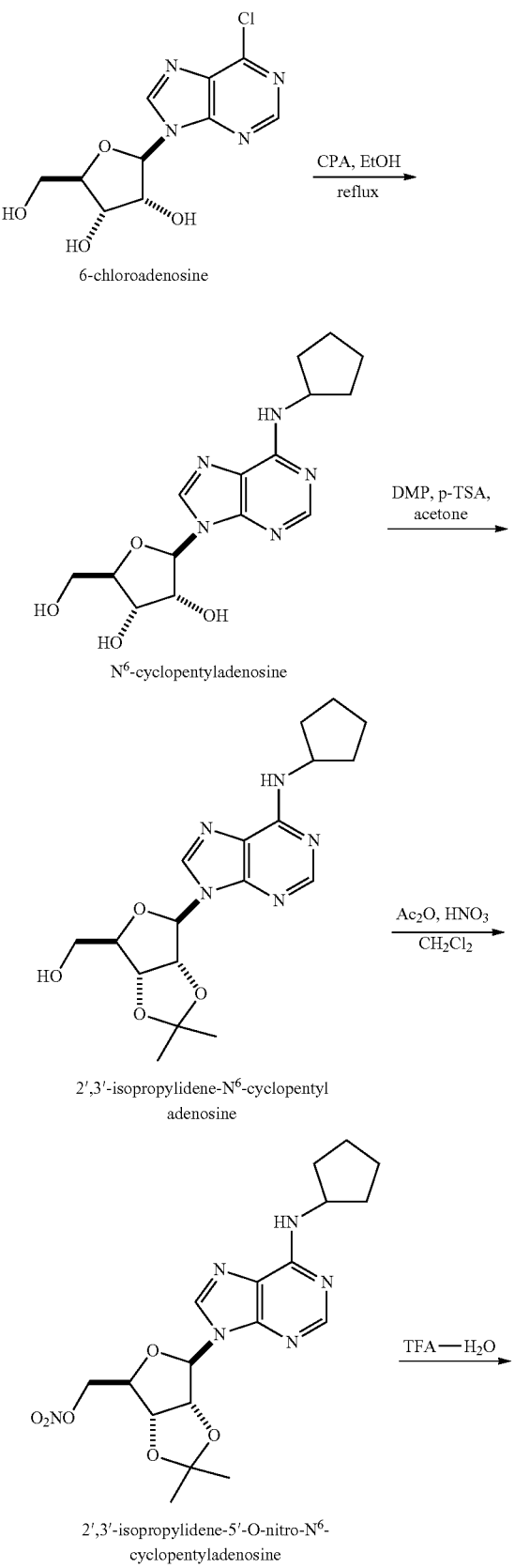

-continued

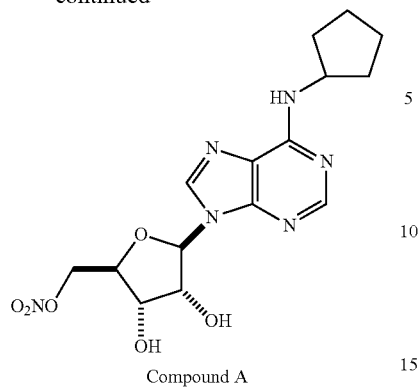

Compound A

Example 2

Formulation Preparation

The invention provides an ophthalmic formulation comprising an aqueous suspension of fine particles of an $A_1$ agonist. Compound A, in API form was fed into a loop mill at the rate of between 50-70 g per hour and at a mill pressure of 90 psi. The milling process produced fine particles having a range of particle sizes of between 3-7 microns with an average particle size of about 5 microns. It is generally recognized that particle sizes less than 50 microns can be administered topically to the cornea in an ophthalmic formulation without undue irritation to the cornea or ocular tissue. Once Compound A was milled the resulting fine particles were sterilized by a gamma irradiation process. The particles were irradiated at up to 40 kGray (kGy) to sterilize the Compound A.

The suspension batches of Compound A were made at Newport Research in California at room temperature and atmospheric pressure and the batches ranged in volume from 10 mL to 900 mL and in concentration from 0.1% to 3.0% of Compound A. Most batches were produced by the use of a stator-rotor mixer (a high-shear mixer) to provide enough shear to achieve adequate wetting and dispersion of the Compound A aggregates to the primary micronized particles. The specific mixer used was an OMNI MIXER HOMOGENIZER, Model 17105 with 10 mm generator probe for 10 mL batches and 20 mm generator probe for batches of 60-900 mL. Several 10-20 mL batches were prepared by ultrasonication for about 20-30 minutes and that was found to be sufficient for adequate dispersion as determined by microscopic examination.

The steps taken for manufacturing a 100 ml batch of a Compound A ophthalmic suspension formulation were as follows:

1. 60-70 mL of purified water was heated in a glass or stainless steel beaker to about 70° C.
2. Sodium carboxymethylcellulose (NaCMC) was added slowly to the warmed purified water from step 1 and mixed until dissolved.
3. The water and NaCMC mixture was removed from heat and the polysorbate 80, benzalkonium chloride (preferably in solution), sodium phosphate monobasic, edetate disodium and sodium chloride were added (in any order) with mixing to the NaCMC mixture while the mixture was being cooled to room temperature. The mixture was mixed until all ingredients were dissolved.
4. Purified water was added to the mixture to bring the volume up to 90 mL.
5. The pH of the resulting mixture was adjusted to 6.5±0.1 with sodium hydroxide (1-10% solution) and/or hydrochloric acid (1-10% solution).
6. Micronized compound A powder in a quantity to achieve the desired concentration was mixed with a high shear mixer such as an OMNI mixer for about 5-20 minutes. The benzalkonium chloride may also be added after the dispersion of the micronized compound A.
7. Purified water was added to make up the 100 mL and the resulting mixture was mixed to ensure homogeneity.
8. The resulting ophthalmic suspension was then cured at about 40° Celsius for about 96 hours to encourage the conversion of the suspended particles of Compound A in an $A_1$ polymorph form to convert to its more stable $A_2$ polymorph. The nature of polymorphs of Compound A is described in PCT/US2013/23166, the contents of which are incorporated herein in its entirety.
9. To the resulting cured suspension, boric acid at a concentration that would make the final formulation concentration about 0.8% w/v was aseptically added.
10. The resulting aseptic solution was then used to charge ophthalmic containers for stability studies.

Example 3

Formulation 1

The following Formulation was prepared according to the Formulation Preparation Example described above, and the pH was adjusted with sodium hydroxide.

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.015 |
| NaOH/HCl (pH adjustment) | pH 6.5 ± 0.1 |
| Purified Water | q.s. 100.00. |

Example 4

Formulation 2

The following formulation was prepared according to the Formulation Preparation Example described above,

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.005 |
| Polysorbate 80 | 0.05 |
| Phosphate Buffer | 0.12 |
| edetate disodium | 0.03 |
| NaCl | 0.4 |
| NaOH/HCl (pH adjustment) | pH 6.5 ± 0.1 |
| Purified Water | q.s. 100.00. |

Example 5

Formulation 3

The following Formulation was prepared according to the Formulation Preparation Example described above.

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.03 |
| NaCl | 0.4 |
| NaOH/HCl (pH adjustment) | pH 6.5 ± 0.1 |
| Purified Water | q.s. 100.00. |

Example 6

Formulation 4

The following Formulation was prepared according to the Formulation Preparation Example described above.

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.015 |
| Polysorbate 80 | 0.05 |
| Phosphate Buffer | 0.12 |
| edetate disodium | 0.03 |
| NaCl | 0.4 |
| NaOH/HCl (pH adjustment) | pH 6.5 ± 0.1 |
| Purified Water | q.s. 100.00. |

Example 7

Formulation 5

The following Formulation was prepared according to the Formulation Preparation Example described above.

| Ingredient | %, w/v |
| --- | --- |
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.06 |
| NaCl | 0.4 |
| NaOH/HCl (pH adjustment) | pH 6.5 ± 0.1 |

Example 8

Formulation 6

It is to be appreciated that any one of the formulations above could also be spiked with and additional ophthalmic agent, for example, latanoprost. Latanoprost has been used as a topical ophthalmic medication for controlling the progression of glaucoma or ocular hypertension by reducing intraocular pressure. It is a prostaglandin analogue that works by increasing the outflow of aqueous fluid from the eyes (through the uveoscleral tract). Latanoprost, which is marketed as Xalatan™ is indicated for the reduction of elevated intraocular pressure in patients with open-angle glaucoma or ocular hypertension. Pre-clinical studies have shown that the use of Compound A in combination with latanoprost provided a significant IOP reduction in normotensive monkeys (US 2011-0172177).

Latanoprost is added, usually aseptically, to the Formulation after the curing step or after all other formulation steps as described above. For example latanoprost can be spiked into Formulation 3 with Compound A at 3.0% (Example 5 above) to prepare a unit dosage of a combination of Compound A with a concentration of latanoprost of about 50 ug/ml. A stability study has been done to study the stability of a combination of a suspension of Compound A as Formulation 3 and latanoprost. The stability study is described below.

Stability Sample Preparation:

A 10 mL sample of a 3% suspension of Compound A spiked with latanoprost at 50 µg/mL was used for the stability study. Ethanol was used to disperse the latanoprost into the suspension of Compound A. The final solution ethanol target was 0.5% so for 10 mLs of the suspension, the latanoprost was dissolved in 50 µL of ethanol.

For 10 mls of the suspension, 0.5 mg of latanoprost was needed for the spike. A 50 µL sample of a commercial solution containing 10 mg/mL of latanoprost in methyl acetate was taken and the solvent removed under vacuum. The residue was taken up in 50 µL of ethanol.

A 9.950 mL sample of the suspension, taken with a 5 mL autopipette (2×4.975 mL) was spiked with the ethanol solution with mixing.

After taking a 500 µL T0 sample, the bulk solution was divided into 3 containers that were set down at 2-8° C., 25° C./60RH and 40° C./75RH.

It was noted on the transfer that the total volume of the suspension was 8.5 mls instead of 10 mL suggesting that the 5 ml auto-pipette used for the sampling encountered issues with measuring the suspension. The solution in this case would be 0.5 mg in 8.5 mL volume or 58.8 µL/mL of latanoprost in the suspension. Therefore for analysis, the theoretical latanoprost in solution after a 50% dilution with acetonitrile was 29.4 µg/mL.

Calibration Curve for Latanoprost

Latanoprost calibration curve samples were prepared by taking a 25 µL sample of the 10 mg/mL solution of latanoprost in methyl acetate. After solvent removal the residue was taken up in 300 µL of ethanol.

Three aliquots were removed from the ethanol solution: 45, 60 and 75 µL. After solvent removal the residues were taken up in 1 mL of acetonitrile with contained 0.5% ethanol. The resultant concentrations were 37.5, 50 and 62.5 µg/mL of latanoprost.

For analysis, these solutions were dissolved in 50% water to give approximately 18.75, 25 and 31.25 µg/mL of latanoprost respectively.

The standards preparation was repeated for each time point and gave good linearity and consistent area counts.

Table 1 below shows the area count data for each concentration and time point with the fluorescent detector. (The areas are the average of 2 injections)

Latanoprost Area Counts

TABLE 1

| Time Points - Calibration Area Counts | | | |
|---|---|---|---|
| | 18.75 μg/ml | 25 μg/ml | 31.25 μg/ml |
| T0 | 63.3 | 87.3 | 114.75 |
| 2 Weeks | 66.65 | 89.5 | 111.2 |
| 4 Weeks | 66.45 | 89.05 | 109.9 |
| 3 months | 63.7 | 85.3 | 111.1 |

Calibration Curve for Latanoprost Acid

A calibration curve of latanoprost acid was also prepared using the commercial solution that contained 10 mg/mL in methyl acetate.

In contrast to the latanoprost standards, these solutions were prepared in 100% acetonitrile.

The solutions injected were 5, 2.5 and 1.25 μg/mL solutions.

Assay Results:

The stability samples were prepared by vortex mixing and sonication of the suspension followed by a 50% dilution with acetonitrile. After centrifugation the supernatant was injected on the HPLC.

The assay results are shown below in Table 2 where the calculated concentration is shown in μg/mL. (The theory concentration is 29.4 μg/ml),

TABLE 2

| | Assay (ug/ml) | | | |
|---|---|---|---|---|
| Latanoprost Assay Results | T0 | 2 Weeks (% T0) | 4 Weeks (% T0) | 3 Months (% T0) |
| 2-8° C. | 29.49 | 32.29 (109%) | 33.97 (115%) | 35.63* (121.1%) |
| 25° C./60 | 29.49 | 32.37 (110%) | 32.90* (112%) | 30.42* (103.5%) |
| 40° C./75 | 29.49 | 31.35 (106%) | 29.90* (101%) | 26.18* (89.0%) |

*Sample contained some latanoprost impurities, such as latanoprost acid.

Purity:

No latanoprost acid was present in the T0, 2 week and 2-8° C. 4 week samples. For the 4 week 25° C./60 and 40° C./75 samples the calculated latanoprost acid values were 0.4 and 0.3 μg/mL respectively. The impurities increased slightly at 3 months. For the 3 month 25° C./60 and 40° C./75 samples the calculated latanoprost acid values were 0.63 and 3.92 μg/mL respectively. For the 3 month 2-8° C. the impurity peak was too small to integrate.

Except for the 40° C./75 sample at 3 months the values for all other samples were below the calibration curve concentrations and therefore below the detection level of the method.

Although the assays of latanoprost especially between 2-8° C. and 25° C./60 were almost identical, impurity peaks in the FLD and UV increase with time and temperature.

The 4 week samples gave the highest impurity peaks followed by the 2 week samples and T0. The 2-8° C. samples had the least amount of changes.

Example 9

Stability Studies

The formulation prepared in Formulation Example 5 was studied for stability over a 6 month period at 5° C. Samples were taken at 1 month, 2 months, 3 months, 6 months, 9 months, 12 months and 18 months and analyzed by liquid chromatography. The stability findings are summarized below.

Formulation Example 5 this formulation has shown chemical stability and no significant particle size changes after 18 months at 5° C. Stability Results for Formulation Example 5.

| Time at 5° C. | Assay % Label Claim | Total Impurities % Label Claim | pH | Particle size distribution |
|---|---|---|---|---|
| 0 | 98 | 0.2% | 6.439 | $X_{10}$ = 1.335 μm<br>$X_{50}$ = 9.805 μm<br>$X_{90}$ = 19.983 μm |
| 1 month | 98 | 0.2% | NT | $X_{10}$ = 1.304 μm<br>$X_{50}$ = 9.622 μm<br>$X_{90}$ = 19.236 μm |
| 3 month | 98 | 0.2% | 6.5 | $X_{10}$ = 1.379 μm<br>$X_{50}$ = 9.955 μm<br>$X_{90}$ = 21.406 μm |
| 6 month | 99 | 0.3% | 6.5 | $X_{10}$ = 1.392 μm<br>$X_{50}$ = 10.273 μm<br>$X_{90}$ = 23.728 μm |
| 9 month | 96.5 | 0.3% | NT | $X_{10}$ = 1.454 μm<br>$X_{50}$ = 10.360 μm<br>$X_{90}$ = 23.022 μm |
| 12 month | 98.6 | 0.3% | 6.4 | $X_{10}$ = 1.414 μm<br>$X_{50}$ = 9.969 μm<br>$X_{90}$ = 20.255 μm |
| 18 month | 97.6 | 0.5% | 6.4 | $X_{10}$ = 1.408 μm<br>$X_{50}$ = 10.281 μm<br>$X_{90}$ = 23.037 μm |

Large Scale Formulation Preparation Example

A total volume of 7.6 liters of the formulation was prepared at a strength of 1.5% Compound A, from 5.7 liters of Formulation Part 1 (see the Table 1 below) which was prepared and cured with stirring at 40° C. for 72 hours to convert the suspended, micronized active pharmaceutical ingredient (API) to its more stable polymorph. This was followed by adding 1.9 liters of Part 2 of the formulation (see Table 2 below) containing Boric Acid which stabilized the suspended API particles. A 5% API overage was used to achieve the target API concentration in the suspension after the formulation was filled into eyedropper bottles.

Instructions for Preparation of 5.7 Liters of Part 1 of Formulation:

The ingredients for Part 1 of the formulation are listed in Table 1 below. Note that the concentrations of the ingredients in Part 1 were adjusted such that the final target concentrations were achieved only after combining with Part 2 of the formulation.

TABLE 1

| Formulation Part 1 Ingredients Formulation: Part 1 | | |
|---|---|---|
| Ingredient | Concentration (% w/v) in Part 1 | Final Concentration (% w/v) in Product |
| Sodium Chloride (NF) | 0.53 | 0.4 |
| Carboxymethyl Cellulose Sodium (USP) | 0.70 | 0.7 |
| Polysorbate 80 (NF) | 0.067 | 0.05 |
| Benzalkonium Chloride, 50% (NF) | 0.0133 | 0.01 |
| Sodium Phosphate Monobasic (USP) | 0.16 | 0.12 |

TABLE 1-continued

Formulation Part 1 Ingredients
Formulation: Part 1

| Ingredient | Concentration (% w/v) in Part 1 | Final Concentration (% w/v) in Product |
|---|---|---|
| Ethylenediaminetetraacetate Disodium (Dihydrate) (USP) | 0.04 | 0.03 |
| Sodium Hydroxide (NF) | 1N | NA |
| Water for Injection (USP) | QS to Volume | NA |

250 mL of IN NaOH solution was prepared for pH adjustment. Polysorbate 80 was dissolved in 200 mL of room temperature water for injection (WFI). Benzalkonium Chloride 50% (BAK) was pre-dissolved in approximately 600 mL of room temperature WFI. 2800±100 g of 70° C. WFI was added to a tared compounding vessel. With stirring, Sodium Carboxymethyl Cellulose was sprinkled into the compounding container, and the CMC container was rinsed 3 times with approximately 200 mL WFI and added to the compounding vessel. The resulting solution was stirred for at least 30 minutes until the solution was visibly clear. 2800±100 g of room temperature WFI was added and stirred until the solution temperature was at or below 35° C. The Sodium Phosphate Monobasic was added to the compounding container, and the Sodium Phosphate Monobasic container was rinsed 3 times with approximately 100 mL WFI and added to the compounding vessel. The Sodium Phosphate Monobasic was stirred until completely dissolved. Ethylenediaminetetraacetate Disodium (EDTA) was added to the compounding container, and the EDTA container was rinsed 3 times with approximately 100 mL WFI and added to the compounding vessel. The solution was stirred until the EDTA was completely dissolved. The pre-dissolved Polysorbate 80 was added to the compounding container, and the container rinsed 3 times with approximately 100 mL WFI and added to the compounding vessel. The resulting solution was mixed for at least 3 minutes. The pre-dissolved BAK was added to the compounding container, the BAK container was rinsed 3 times with approximately 100 mL WFI and added to the compounding vessel and mixed for at least 3 minutes. The sodium chloride (NaCl) was added to the compounding container, and the NaCl container was rinsed 3 times with approximately 200 mL WFI and added to the compounding vessel. The compound vessel was mixed till the NaCl was completely dissolved. WFI was added to the compounding vessel to achieve the target weight of 8550±50 g (approximately 95% of final QS weight). A 5 mL aliquot of the bulk solution was removed for pH testing. If necessary, 10 mL portions of 1N NaOH were added to the bulk solution until a pH of 6.5±0.1 was achieved, mixing a minimum of 3 minutes between NaOH additions. QS to 9000±50 g with room temperature WFI.

Utilizing aseptic manufacturing conditions, a sterile, 10-liter, stainless steel, temperature-controlled formulation vessel equipped with impeller for stirring was charged with 120 g (for 7.6 L of 1.575% Compound A, including a 5% overage) of gamma sterilized, micronized Compound A API. Next, 4000 g of the Part 1 solution was passed through a wetted and purged sterile filter and delivered aseptically to the formulation vessel. The vessel was stirred at 2000±50 rpm for 20 minutes to uniformly suspend the micronized API in the Part 1 solution. A final aliquot of 1780 g of Part 1 formulation was sterile filtered into the formulation vessel to wash any unsuspended API into the bulk solution and produce a final tared weight of 5700 g. After stirring at 2000±50 rpm for 20 minutes to homogenize the suspension, the stirring speed was reduced to 600 rpm±50 and the heater/recirculation pump was set to 40° C. to begin heating the solution to 40° C.±5° C. Once the suspension reached the target temperature the suspension was stirred for 72 hours. Instructions for Preparation of 4.0 Liters of Part 2 of Formulation:

The ingredients for Part 2 of the formulation are listed in Table 2 below. Note that the concentrations of the ingredients in Part 2 are adjusted such that the final target concentrations are achieved only after combining with Part 1 of the formulation.

TABLE 2

Formulation Part 2 Ingredients
Formulation: Part 2

| Ingredient | Concentration (% w/v) in Part 1 | Final Concentration (% w/v) in Drug Product |
|---|---|---|
| Carboxymethyl Cellulose Sodium (USP) | 0.70 | 0.7 |
| Boric Acid (NF) | 3.2 | 0.8 |
| Sodium Hydroxide (NF) | 1N | NA |
| Water for Injection (USP) | QS to Volume | NA |

Add 2500±100 g of 70° C. WFI to a tared compounding vessel. With stirring, Sodium Carboxymethyl Cellulose was sprinkled into the compounding container, and the CMC container was rinsed 3 times with approximately 100 mL WFI and added to the compounding vessel. The solution was stirred for at least 30 minutes until the solution was visibly clear. 900±100 g of room temperature WFI and was added and the solution stirred until the CMC was completely dissolved. The Boric acid was added to the vessel, and the boric acid container rinsed at least 3 times with 100 mL WFI and the rinses were added to the vessel. When the solution was at or below 25° C., 40 mL of IN NaOH was added and stirred for 5 minutes before checking and recording the pH. WFI was added to the vessel to a final QS weight of 4000±50 g and mixed for a minimum of 15 minutes. The heater on the 10-liter formulation vessel (after the curing period) was turned off and cooling water was circulated. Stirring continued at approximately 600 rpm. 1900 g of the Part 2 formulation was slowly added aseptically through a wetted and purged sterile filter to achieve a final QS formulation weight of 7600 g (see FIG. 1). The resulting solution was stirred at 2000±50 rpm for 20 minutes. With constant stirring, 5.0-5.6 g (target 5.3 g) of the suspension formulation were filled into 10 mL gamma-sterilized Rexam eye dropped bottles. The bottles were closed with matching dropper tips and caps.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

The invention claimed is:

1. An ophthalmic formulation comprising the following ingredients as % (w/v):

| | |
|---|---|
| Compound A, micronized | 0.5-3.0 |
| Sodium CMC, low viscosity | 0.7 |
| Boric Acid | 0.8 |
| Benzalkonium Chloride | 0.005-0.02 |
| Polysorbate 80 | 0.05 |
| Phosphate Buffer | 0.12 |
| edetate disodium | 0.015-0.06 |
| NaCl | 0.4 |
| NaOH/HCl sufficient % to adjust pH to | 6.5 ± 0.1, |
| Purified Water | q.s. 100.00, | wherein Compound A is ((2R,3S,4R,5R)-5-(6-(cyclopentylamino)-9H-purin-9-yl)-3,4-dihydroxytetrahydrofuran-2-yl)methyl nitrate and sodium CMC is sodium carboxymethyl cellulose.

2. An ophthalmic formulation comprising the following ingredients as % (w/v):

| | |
|---|---|
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.015 |
| NaOH/HCl sufficient % to adjust pH to | 6.5 ± 0.1 |
| Purified Water | q.s. 100.00. |

3. An ophthalmic formulation comprising the following ingredients as % (w/v):

| | |
|---|---|
| Compound A, micronized | 0.5-3.0 |
| Sodium CMC, low viscosity | 0.70 |
| Boric Acid | 0.8 |
| Benzalkonium Chloride | 0.005 |
| Polysorbate 80 | 0.05 |
| Phosphate Buffer | 0.12 |
| edetate disodium | 0.03 |
| NaCl | 0.4 |
| NaOH/HCl sufficient % to adjust pH to | 6.5 ± 0.1 |
| Purified Water | q.s. 100.00. |

4. An ophthalmic formulation comprising the following ingredients as % (w/v):

| | |
|---|---|
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.03 |
| NaCl | 0.4 |
| NaOH/HCl sufficient % to adjust pH to | 6.5 ± 0.1 |
| Purified Water | q.s. 100.00. |

5. An ophthalmic formulation comprising the following ingredients as % (w/v):

| | |
|---|---|
| Compound A, micronized | 0.5-3.0 |
| Sodium CMC, low viscosity | 0.70 |
| Boric Acid | 0.8 |
| Benzalkonium Chloride | 0.015 |
| Polysorbate 80 | 0.05 |
| Phosphate Buffer | 0.12 |
| edetate disodium | 0.03 |
| NaCl | 0.4 |
| NaOH/HCl sufficient % to adjust pH to | 6.5 ± 0.1 |
| Purified Water | q.s. 100.00. |

6. An ophthalmic formulation comprising the following ingredients as % (w/v):

| | |
|---|---|
| Compound A, micronized | 0.5-3.0 |
| Sodium CMC, low viscosity | 0.70 |
| Boric Acid | 0.8 |
| Benzalkonium Chloride | 0.01 |
| Polysorbate 80 | 0.05 |
| Phosphate Buffer | 0.12 |
| edetate disodium | 0.06 |
| NaCl | 0.4 |
| NaOH/HCl sufficient % to adjust pH to | 6.5 ± 0.1 |
| Purified Water | q.s. 100.00. |

7. The formulation of any one of claims 1-6, further comprising a second therapeutic ophthalmic agent.

8. The formulation of claim 7, wherein the second ophthalmic agent is selected from the group comprising prostaglandin analogs, β-blockers, carbonic anhydrase inhibitors, rho-kinase inhibitors, $\alpha_2$ adrenergic agonists, miotics, neuroprotectants, adenosine $A_3$ antagonists, adenosine $A_{2A}$ agonists, ion channel modulators and combinations thereof.

9. The formulation of claim 7, wherein the second ophthalmic agent is a prostaglandin analog.

10. The formulation of claim 9, wherein the prostaglandin analog is latanoprost.

11. The formulation of claim 10, wherein the latanoprost is present between about 1-200 µg/ml.

12. The formulation of claim 11, wherein the latanoprost is present in about 50 µg/ml.

13. A kit or packaged formulation comprising a topically applicable ophthalmic formulation as in any one of claims 1-6.

* * * * *